(12) United States Patent
Balentine

(10) Patent No.: US 12,295,871 B2
(45) Date of Patent: May 13, 2025

(54) UNIVERSAL KNEE BRACE HANDLE

(71) Applicant: Imprint Performance, LLC, Hoover, AL (US)

(72) Inventor: Bryan Balentine, Birmingham, AL (US)

(*) Notice: Subject to any disclaimer, the term of this patent is extended or adjusted under 35 U.S.C. 154(b) by 0 days.

(21) Appl. No.: 17/779,543

(22) PCT Filed: Nov. 23, 2020

(86) PCT No.: PCT/US2020/061741
§ 371 (c)(1),
(2) Date: May 24, 2022

(87) PCT Pub. No.: WO2021/108287
PCT Pub. Date: Jun. 3, 2021

(65) Prior Publication Data
US 2023/0000656 A1     Jan. 5, 2023

Related U.S. Application Data

(60) Provisional application No. 62/939,780, filed on Nov. 25, 2019.

(51) Int. Cl.
*A61F 5/01* (2006.01)

(52) U.S. Cl.
CPC .................. *A61F 5/0123* (2013.01)

(58) Field of Classification Search
CPC ....... A61F 5/0123; A61F 5/0109; B25G 3/00; B25G 3/02; B25G 3/04; B25G 3/06; B25G 3/08; B25G 3/10; B25G 3/12; B25G 3/14; B25G 3/20; B25G 3/24; B25G 3/26; B25G 3/30; B25G 3/36; B25G 3/38; A45C 13/22; A45C 2013/223; A45F 2005/1053; A45F 5/1026; A45F 5/1046; A45F 2005/1033; A45F 2005/104; A45F 5/10; A45F 5/102; A45F 2005/1006; A45F 2005/1013; A45F 2005/106; A45F 2005/1066;
(Continued)

(56) References Cited

U.S. PATENT DOCUMENTS

| | | | | |
|---|---|---|---|---|
| 1,498,508 A | * | 6/1924 | Streckfuss | B65D 23/104 294/31.2 |
| 1,503,348 A | * | 7/1924 | Bruhn | B62D 1/043 74/557 |

(Continued)

OTHER PUBLICATIONS

United States Patent and Trademark Office, International Search Report for International Application No. PCT/US2020/061741, Feb. 12, 2020.

(Continued)

*Primary Examiner* — Jeffrey O'Brien
(74) *Attorney, Agent, or Firm* — Husch Blackwell LLP; Timothy L. Capria; Alexandra C. Lynn

(57) ABSTRACT

A handle includes a handle body including a resiliently biased front cavity member disposed and a rear cavity member, together defining a cavity. The resiliently biased front cavity member and rear cavity member include one or more grooves disposed thereon. The cavity is configured to receive a portion of a knee brace. The knee brace may be selected, secured, and removed from cavity by moving the resiliently biased front cavity member. The front cavity member may be secured by using a releasable fastener.

20 Claims, 8 Drawing Sheets

(58) Field of Classification Search
CPC ... A45F 2005/1073; A47J 45/07; A47J 45/10; B65D 23/104; B65D 23/106; B65D 23/108
USPC .......................... 16/406, 422, 425, 426, 427
See application file for complete search history.

(56) References Cited

U.S. PATENT DOCUMENTS

| | | | | | |
|---|---|---|---|---|---|
| 1,539,201 | A * | 5/1925 | Ottow | .................. | B65D 23/108 294/31.2 |
| 1,863,136 | A * | 6/1932 | Hood | .................. | B65D 23/104 248/230.4 |
| 2,409,684 | A * | 10/1946 | Jenkins | .................. | B65D 71/50 294/87.22 |
| 2,602,687 | A * | 7/1952 | Stanley | .................. | B65D 23/108 294/31.2 |
| 2,985,330 | A * | 5/1961 | Buys | .................. | B65D 23/108 215/397 |
| 3,072,955 | A * | 1/1963 | Mitchell | .................. | A45F 5/10 294/171 |
| 3,120,974 | A * | 2/1964 | Matson | .................. | A45F 5/10 215/396 |
| 3,155,263 | A * | 11/1964 | Hidding | .................. | B65D 23/108 215/397 |
| 3,275,366 | A * | 9/1966 | Hidding | .................. | B65D 23/108 215/396 |
| 3,311,252 | A * | 3/1967 | Swartwood | .................. | B65D 23/108 D9/434 |
| 3,339,814 | A * | 9/1967 | Carbine | .................. | B65D 71/50 215/396 |
| 3,463,536 | A * | 8/1969 | Beyer | .................. | A47J 45/077 215/396 |
| 3,502,071 | A * | 3/1970 | Holly | .................. | A61H 3/00 601/34 |
| 4,059,209 | A * | 11/1977 | Grisel | .................. | A63C 11/009 294/143 |
| 4,523,781 | A * | 6/1985 | Brody | .................. | A46B 5/02 401/6 |
| 4,579,237 | A * | 4/1986 | Gagnon | .................. | B65D 23/104 215/396 |
| 4,696,505 | A * | 9/1987 | Shadoan | .................. | A45F 5/1026 294/167 |
| 4,794,667 | A * | 1/1989 | Nelson | .................. | B25G 1/00 294/58 |
| 5,441,323 | A * | 8/1995 | Goddard | .................. | A45F 5/1026 294/166 |
| 5,667,265 | A * | 9/1997 | Gebhard | .................. | B65D 23/108 294/169 |
| 5,752,732 | A * | 5/1998 | Beaton | .................. | B65D 23/104 294/169 |
| 5,779,655 | A * | 7/1998 | Holden | .................. | A61F 5/0111 602/5 |
| 5,855,403 | A * | 1/1999 | Harper | .................. | A45F 5/1026 294/166 |
| 5,870,800 | A * | 2/1999 | Chao | .................. | B62D 1/043 16/422 |
| 5,890,635 | A * | 4/1999 | Wu | .................. | B65D 23/108 224/257 |
| 6,223,372 | B1 * | 5/2001 | Barber | .................. | F16B 45/023 7/118 |
| 6,394,517 | B1 * | 5/2002 | Borg | .................. | B65D 23/108 215/397 |
| 7,014,232 | B2 * | 3/2006 | Bosa | .................. | A01B 1/026 294/58 |
| 7,047,604 | B2 * | 5/2006 | Axel | .................. | F16B 45/04 294/158 |
| 7,108,128 | B2 * | 9/2006 | Borg | .................. | A45F 5/10 294/87.2 |
| 7,328,925 | B1 * | 2/2008 | Jenkins | .................. | A45F 5/1026 294/159 |
| 7,657,972 | B2 * | 2/2010 | Jenkins | .................. | B25G 1/06 16/108 |
| 8,381,358 | B1 * | 2/2013 | Frey | .................. | B25G 1/06 16/444 |
| 8,621,719 | B2 * | 1/2014 | Nakashima | .................. | B25F 5/026 16/422 |
| 8,671,523 | B1 * | 3/2014 | Day | .................. | A45F 5/10 16/422 |
| 8,851,234 | B2 * | 10/2014 | Bachorski | .................. | E06C 7/00 294/166 |
| 9,010,279 | B1 * | 4/2015 | Saber | .................. | A01K 27/008 119/702 |
| 9,114,911 | B2 * | 8/2015 | Laib | .................. | B65D 23/106 |
| 9,539,851 | B1 * | 1/2017 | Tanda | .................. | B44D 3/14 |
| 9,708,100 | B2 * | 7/2017 | Meinzinger | .......... | B65D 23/104 |
| 9,834,349 | B1 * | 12/2017 | Gallagher | ............ | B65D 23/108 |
| 10,752,401 | B2 * | 8/2020 | Zhang | .................. | B65D 25/2876 |
| 11,794,329 | B1 * | 10/2023 | Pladson | .................. | B25G 3/36 |
| 2005/0167289 | A1 * | 8/2005 | Borg | .................. | B65D 23/104 294/87.2 |
| 2005/0205436 | A1 * | 9/2005 | Erickson | .............. | B65D 23/108 206/139 |
| 2007/0209162 | A1 * | 9/2007 | McRoberts | ............. | B25F 5/026 16/426 |
| 2011/0173778 | A1 * | 7/2011 | Wales | .................. | B25G 3/20 16/426 |
| 2013/0008915 | A1 * | 1/2013 | Dorn | .................. | A45F 5/102 220/755 |
| 2014/0024506 | A1 * | 1/2014 | Vixathep | .................. | A63B 21/0726 482/108 |
| 2014/0307452 | A1 * | 10/2014 | Pannekoek | .............. | B25G 3/20 362/396 |
| 2014/0319785 | A1 * | 10/2014 | Chen | .................. | B23B 31/201 279/43.5 |
| 2014/0364782 | A1 | 12/2014 | Knecht | | |
| 2018/0140890 | A1 * | 5/2018 | Sheppard | ........... | A63B 21/0728 |
| 2020/0188155 | A1 * | 6/2020 | Balentine | .............. | A61F 5/0109 |
| 2022/0227533 | A1 * | 7/2022 | Doherty | .................. | A45F 5/102 |
| 2022/0232956 | A1 * | 7/2022 | Ripley | .................. | A45F 3/18 |

OTHER PUBLICATIONS

United States Patent and Trademark Office, Written Opinion of the International Searching Authority for International Application No. PCT/US2020/061741, Feb. 12, 2020.

* cited by examiner

UNIVERSAL KNEE BRACE HANDLE

CROSS-REFERENCE TO RELATED APPLICATION

This application claims the benefit of U.S. Provisional Patent Application No. 62/939,780, filed Nov. 25, 2019, which is incorporated by reference herein in its entirety.

TECHNICAL FIELD

The present disclosure relates to a handle for a knee brace. More specifically, the disclosure is directed towards a handle having a resiliently biased universal fit element for attaching to varying knee braces.

BACKGROUND OF INVENTION

Knee braces, or knee orthoses, are commonly employed to resist excessive movement of the knee joint in humans. In particular, knee braces provide support to the patella and surrounding ligaments. Knee braces are used during physical activity, such as sports, recovering from an injury, and to prevent injury. In instances where a knee brace is used with subjects having diseases causing impairment of muscles surrounding the knee, the knee brace can prevent flexion or extension instability of the knee.

Because knee braces are generally desired to provide stability to the knee without excessively limiting range of motion in the subject, existing knee braces are not positionally secure, or do not allow the subject to adjust the position of the knee brace without excessively limiting range of motion in the subject. Knee braces may be configured with handles such that the subject can retain or adjust the position of the knee braces. However, because knee braces are not uniform in shape, size, and configuration, often differing by manufacturer and model, one handle has not been able to fit knee braces that differ in these ways. Thus, a need exists for a knee brace handle that is adapted to fit with a wide variety of knee braces such that a subject may positionally adjusted or secure knee braces.

BRIEF SUMMARY

In one aspect, a handle includes a body having a top portion, a bottom portion opposite of the top portion, a front side, and a rear side opposite of the front side. The handle includes a resiliently biased front cavity member disposed on the front side of the body and defining a hinge. The resiliently biased front cavity member hingedly pivots between a closed position and an open position. A releasable fastener may be disposed on the handle and configured to secure the resiliently biased front cavity member in the closed position. The releasable fastener may be a thumb screw or a friction fit (not shown). The front cavity member may be configured to open away from the rear side when moving from the closed position to the open position and toward the rear side when moving from the open position to the closed position.

The handle includes a rear cavity member disposed on the rear side of the body and opposite of the resiliently biased front cavity member.

The resiliently biased front cavity member or the rear cavity member may include one or more grooves. Both of the resiliently biased front cavity member and the rear cavity member may include the one or more grooves. Each, or both, of the resiliently biased front cavity member and the rear cavity member may include a first cavity end and a second cavity end opposite of the first cavity end. In embodiments of the handle including the one or more grooves on the resiliently biased front cavity member, the resiliently biased front cavity member may include one or more grooves of the resiliently biased front cavity member comprised of a first groove and a second groove disposed proximate to the first cavity end and the second cavity end, respectively. The first groove and the second groove of the resiliently biased front cavity member may have a triangular profile. The resiliently biased front cavity member may include a third groove and a fourth groove disposed proximate to the first groove and the second groove, respectively, of the front cavity member.

In embodiments of the handle including the one or more grooves on the rear cavity member, the one or more grooves may include a first groove and a second groove each having a triangular profile and disposed at the first cavity end and the second cavity end.

The handle includes a cavity defined by the resiliently biased front cavity member and the rear cavity member. The cavity may be disposed at the bottom portion of the body. The cavity may include a central longitudinal axis. The rear cavity member may include a third groove and a fourth groove disposed proximate to the central longitudinal axis. Each of the third groove and fourth groove may have a rectangular profile.

The handle may include an insert configured to be cooperatively received in the cavity of the handle. The insert may include a slot having a differing inner profile from the inner profile of the cavity. The slot may have a rectangular profile. The insert may include a resiliently biased hinge that allows the insert to move between open and closed positions. The insert may include an upper lip and a bottom lip.

The resiliently biased front cavity member may curve away from the central longitudinal axis. The rear side of the rear cavity member includes an indentation. The body of the handle may be elongated from the top portion to the bottom portion. The body may include a first leg and a second leg extending from the top portion to the bottom portion, and the top portion may include a width that is greater than a width of the first leg and the second leg. The body and/or the insert, including components thereof, may be rigid. The body and/or the insert, including components thereof, may be integrally formed.

BRIEF DESCRIPTION OF DRAWINGS

It should be noted that identical features in different drawings are shown with the same reference numeral.

DETAILED DESCRIPTION

Figure 1:
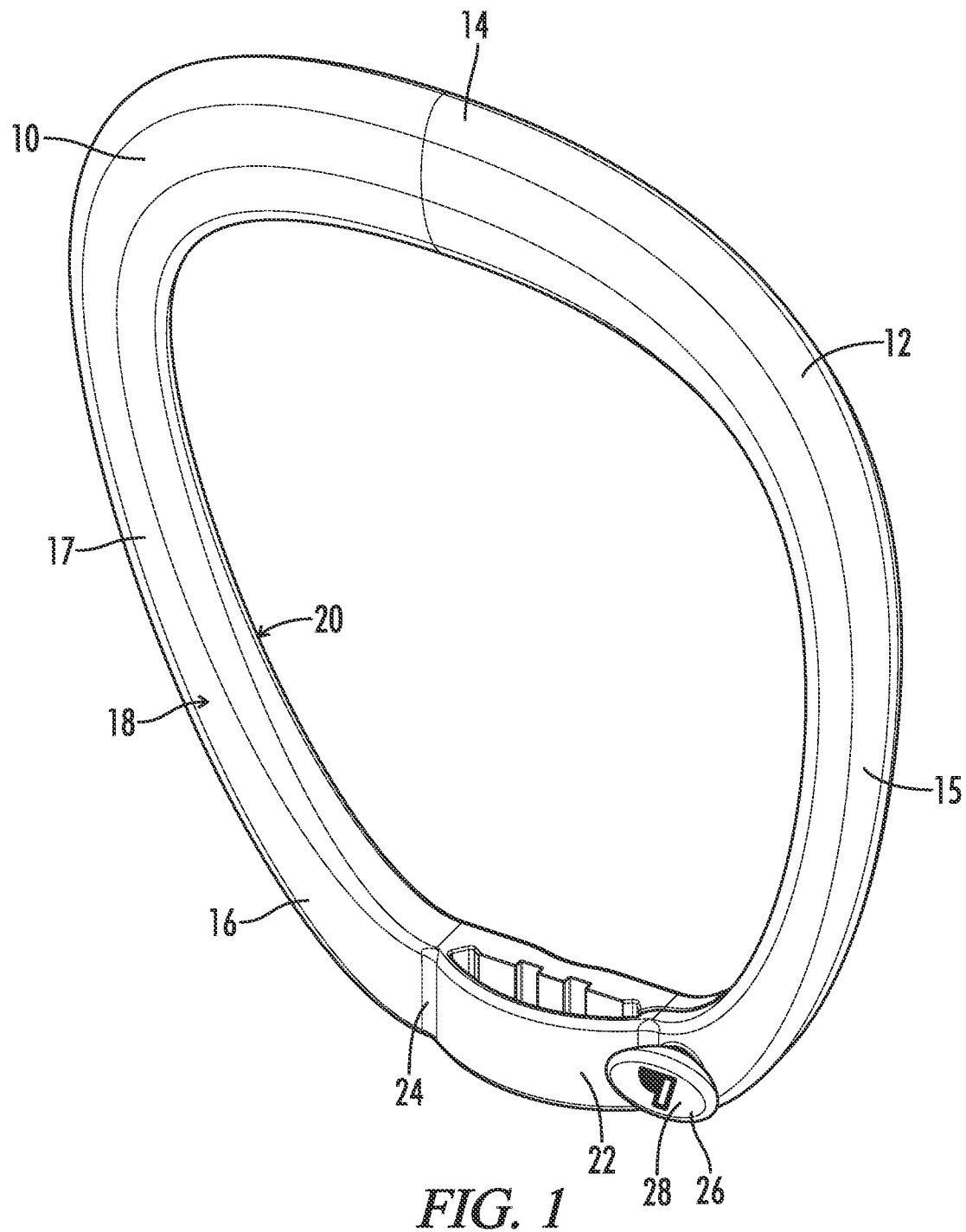
FIG. 1 shows a front perspective view of an embodiment of a handle.

Reference now will be made in detail to the embodiments of the present disclosure. It will be apparent to those of ordinary skill in the art that various modifications and variations can be made to the teachings of the present disclosure without departing from the scope of the disclosure. For instance, features illustrated or described as part of one embodiment can be used with another embodiment to yield a further embodiment.

Thus, it is intended that the present disclosure covers such modifications and variations that come within the scope of the appended claims and their equivalents. Other objects, features, and aspects of the present disclosure are disclosed in or are apparent from the following description. It is to be understood by one of ordinary skill in the art that the present disclosure is a description of exemplary embodiments only and is not intended as limiting the broader aspects of the present disclosure.

For the sake of clarity, not all reference numerals are necessarily present in each drawing Figure. In additional, positional terms such as "upper," "lower," "side," "top," "bottom," "vertical," "horizontal," etc. refer to the handle when in the orientation shown in the drawings. The skilled artisan will recognize that the handle can assume different orientations when in use.

Referring to FIGS. 1-12, a handle 10 for knee braces has been developed. The handle 10 of the present disclosure is intended to fit a wide variety of different knee braces, enabling a subject to retain a position of a knee brace while still allowing the subject to have a comfortable range of motion while wearing the knee brace. The handle 10 enables the user to prevent migration and/or easily adjust a knee brace.

One embodiment of the handle 10 is shown in FIG. 1. In this embodiment, a handle 10 includes a body 12. The body 12 may be constructed of any suitable material, including polymers such as polyethylenes, polypropylene, polyvinyl chloride, polylactic acids, and acrylonitrile butadiene styrene, or metals or metal alloys, such as stainless steel. The body 12 may be constructed of a material that is antiallergenic. The body 12 may be impregnated with an antimicrobial, such as triclosan.

The body 12 includes a top portion 14, a bottom portion 16 opposite of the top portion 14, a front side 18, and a rear side 20 opposite of the front side 18. The top portion 14 may be described as the portion of the handle 10 that extends upwardly (e.g., cranially) with a standing subject when the handle 10 is in-use. The bottom portion 16 may be described as the portion of the handle 10 that extends downwardly (e.g., caudally) with a standing subject when the handle 10 is in-use. The front side 18 may be described as the side of the handle 10 that faces away from the standing subject when the handle 10 is in-use. The rear side 20 may be described as the side of the handle 10 that faces toward the standing subject and a brace when the handle 10 is in-use. The body 12 of the handle 10 may be elongated from the top portion 14 to the bottom portion 16, and the top portion 14 may include a width that is greater than a width of a first leg 15 and a second leg 17.

Figure 2A:
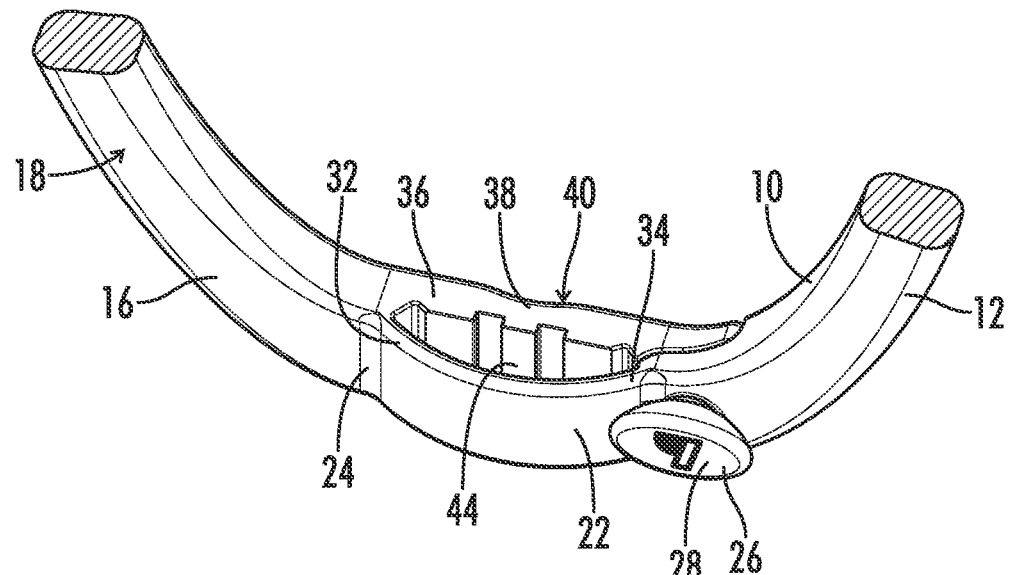
FIG. 2A shows a close-up front perspective view of the handle of FIG. 1 in a closed position.
Figure 2B:
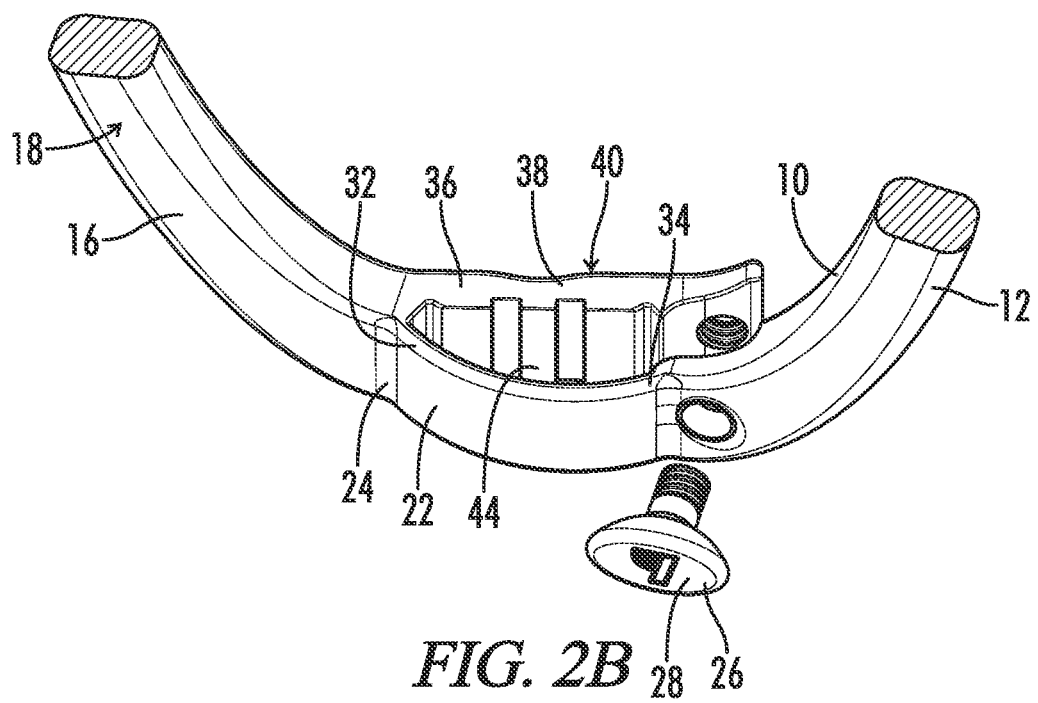
FIG. 2B shows a close-up front perspective view of the handle of FIG. 1 in an open position.
Figure 3:
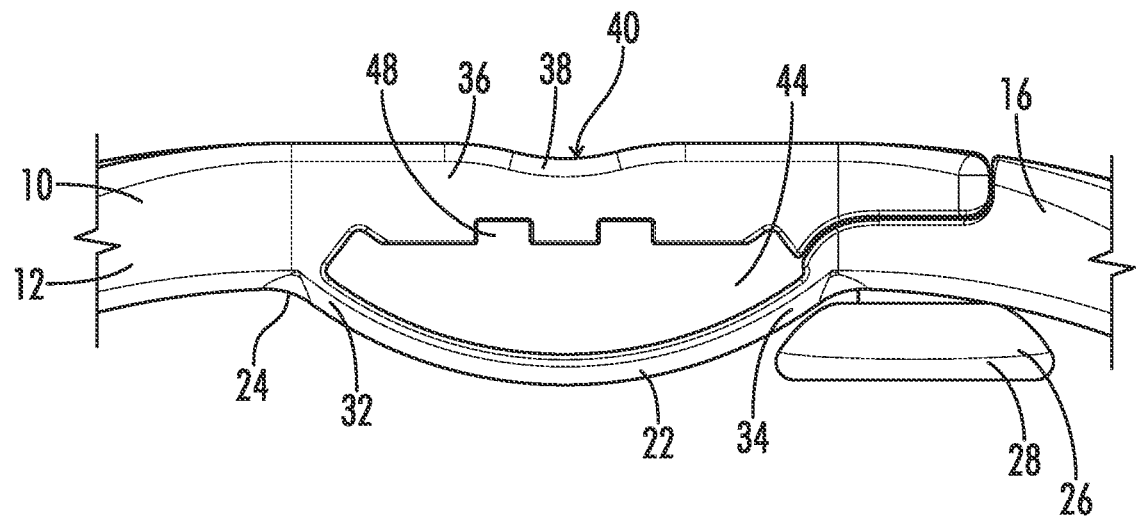
FIG. 3 shows a close-up top view of the bottom portion of the handle of FIG. 1.
Figure 4:
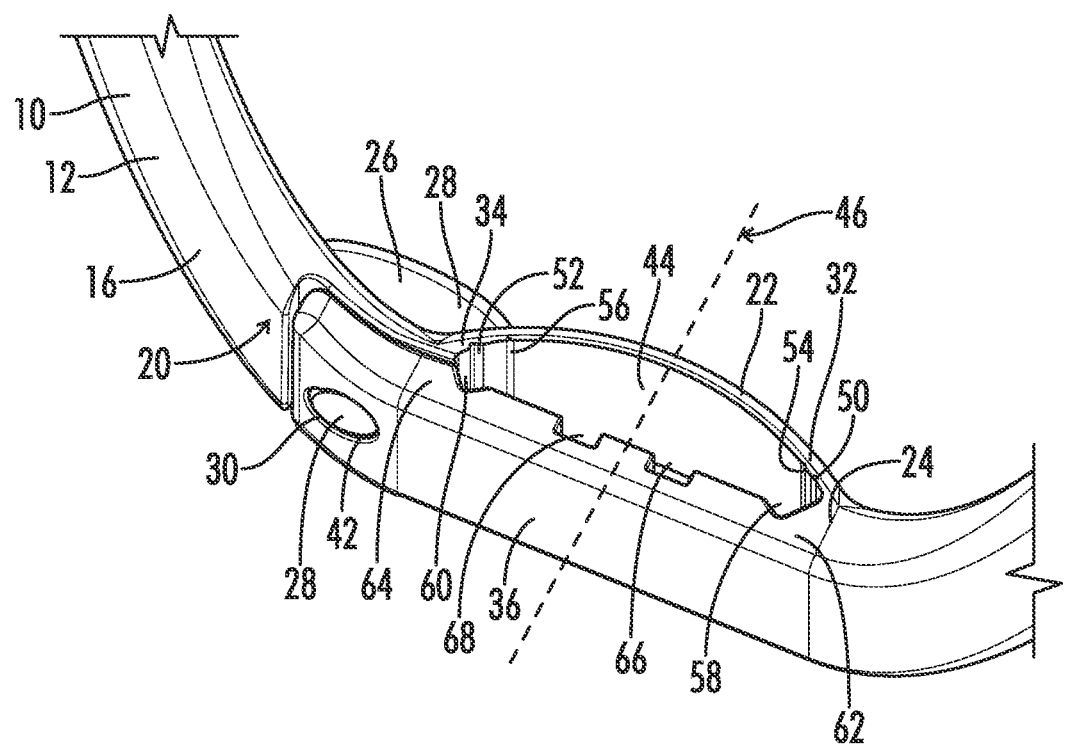
FIG. 4 shows a close-up rear perspective view of the bottom portion of the handle according to another embodiment.
Figure 5:
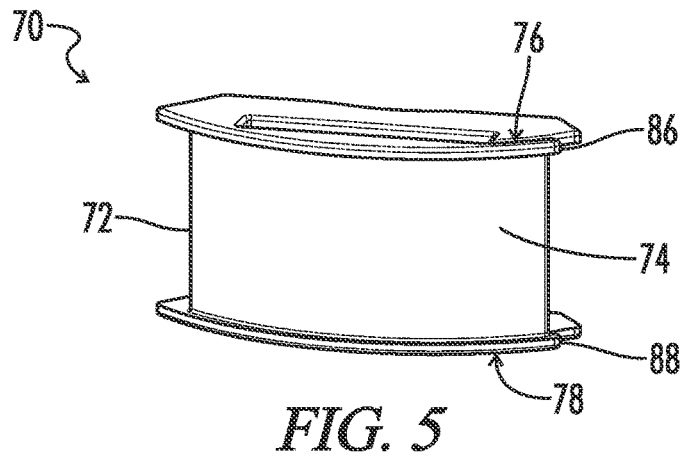
FIG. 5 shows a front perspective view of an insert according to one embodiment of the handle.
Figure 6A:
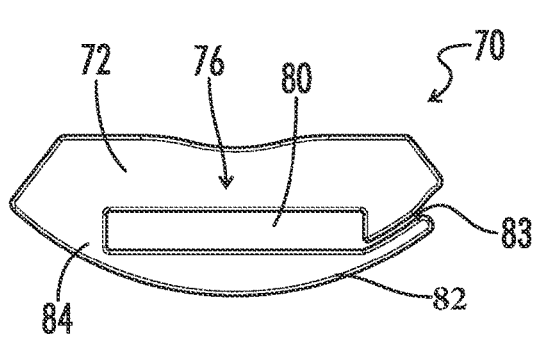
FIG. 6A shows a top view of an insert of FIG. 5 in a closed position.
Figure 6B:
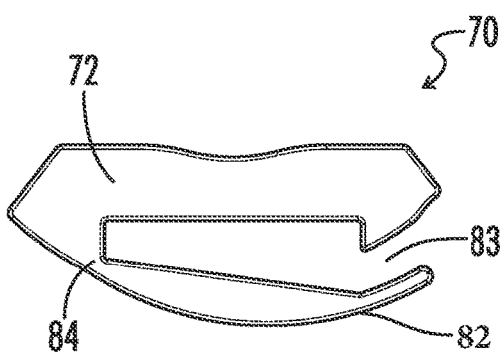
FIG. 6B shows a top view of an insert of FIG. 5 in an open position.
Figure 7:
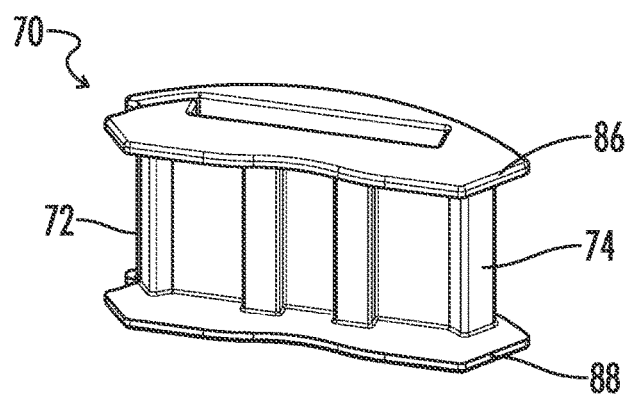
FIG. 7 shows a rear perspective view of an insert of FIG. 5.
Figure 8:
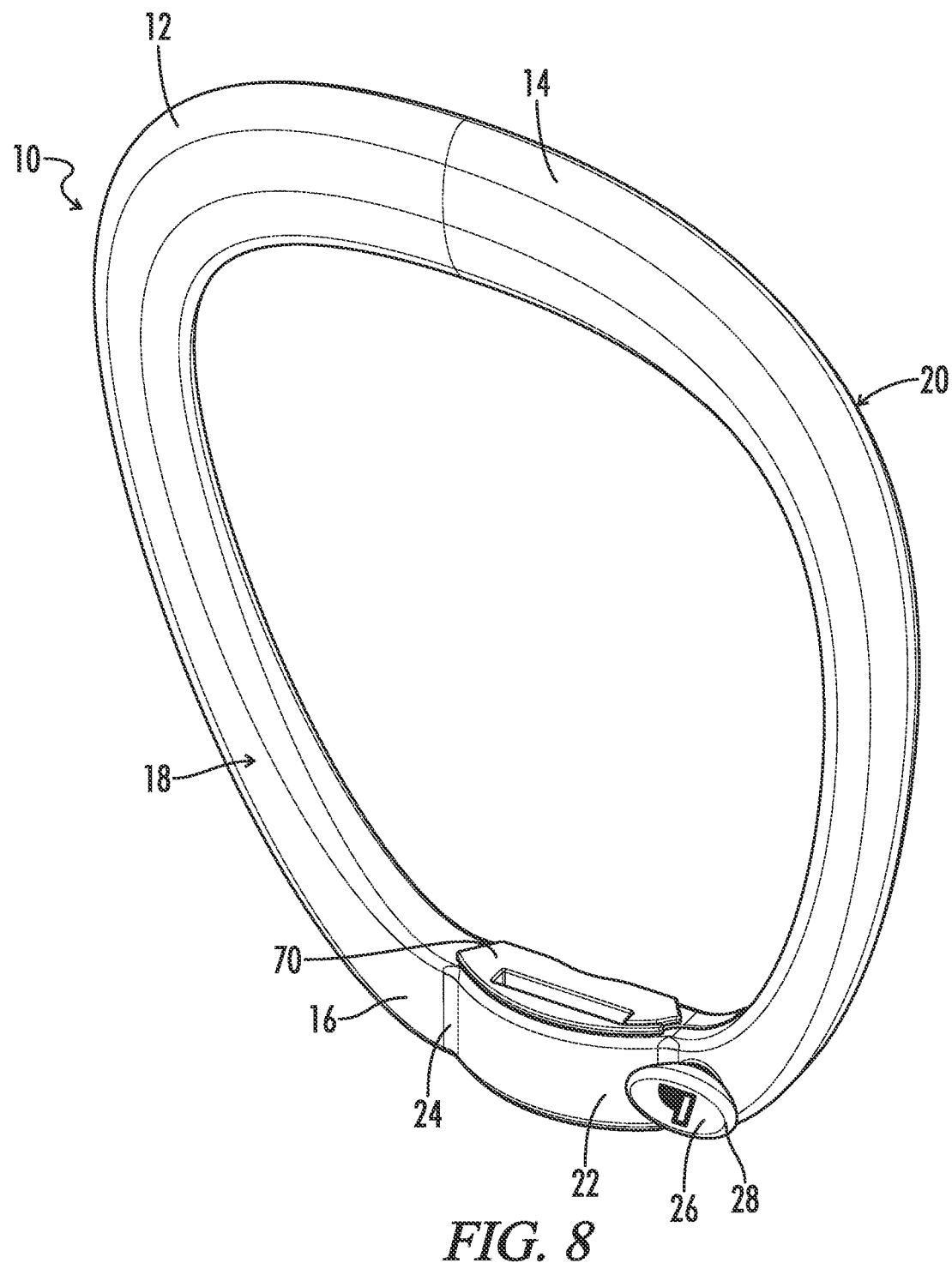
FIG. 8 shows a front perspective view of an embodiment of the handle with the insert disposed within the cavity.
Figure 9A:
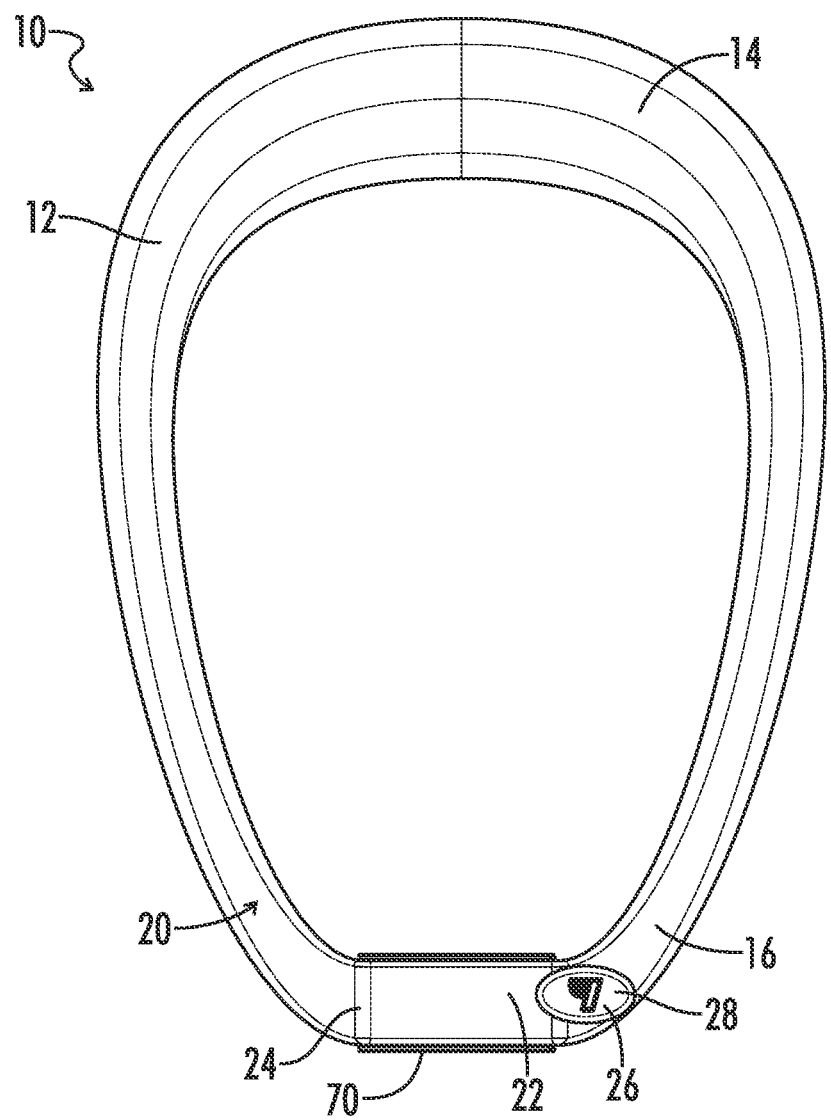
FIG. 9A shows a front view of the handle with the insert of FIG. 8.
Figure 9B:
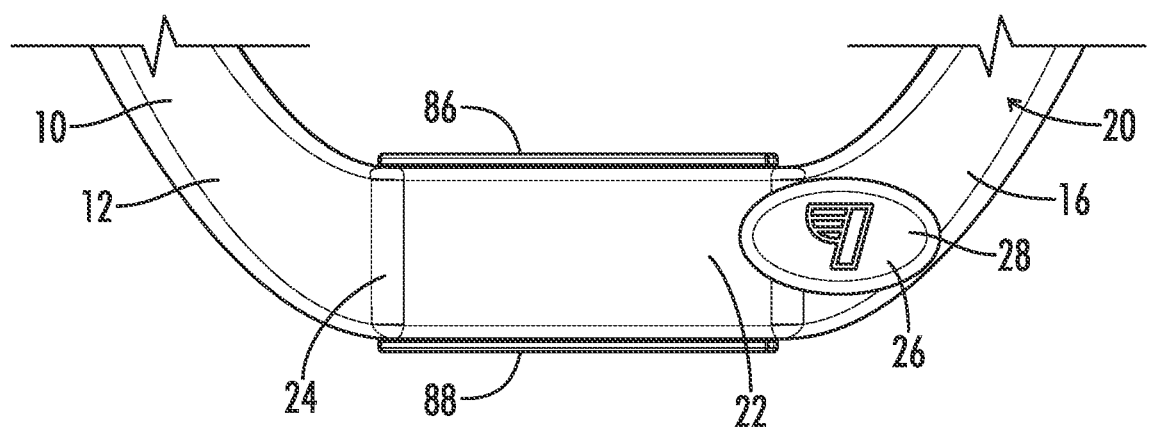
FIG. 9B shows a close-up front view of the handle with the insert of FIG. 8.
Figure 10:
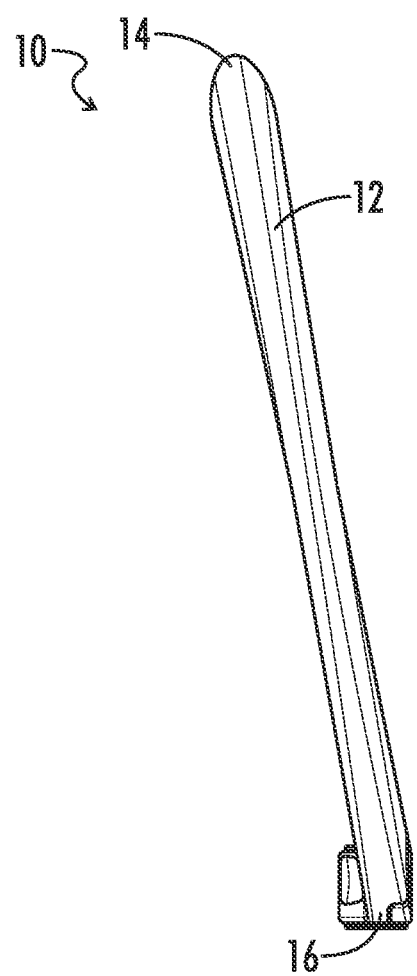
FIG. 10 shows a right-side view of the handle with the insert of FIG. 8.
Figure 11A:
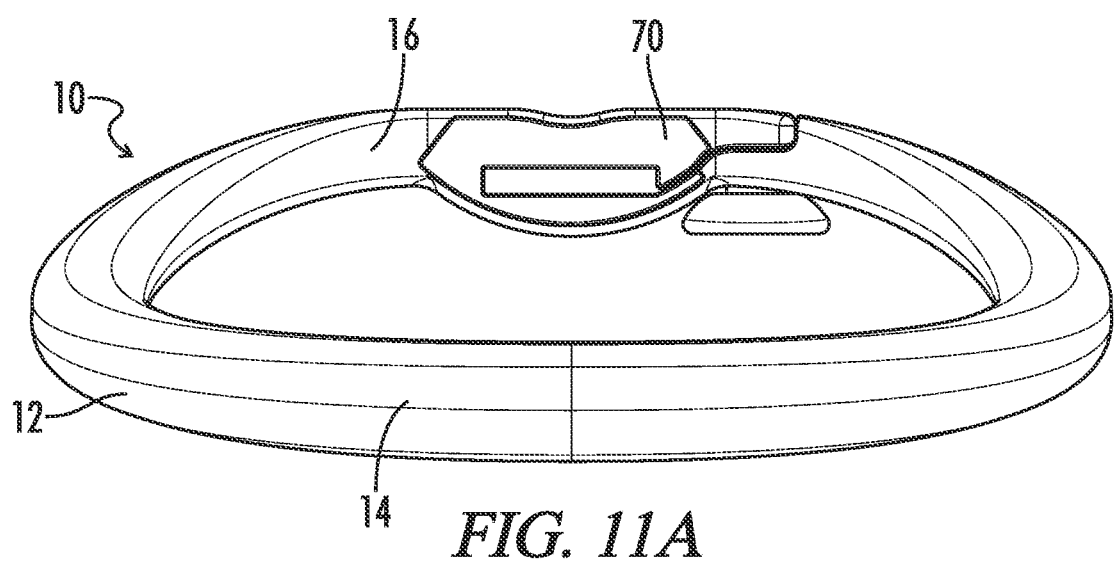
FIG. 11A shows a top perspective view of the handle with the insert of FIG. 8.
Figure 11B:
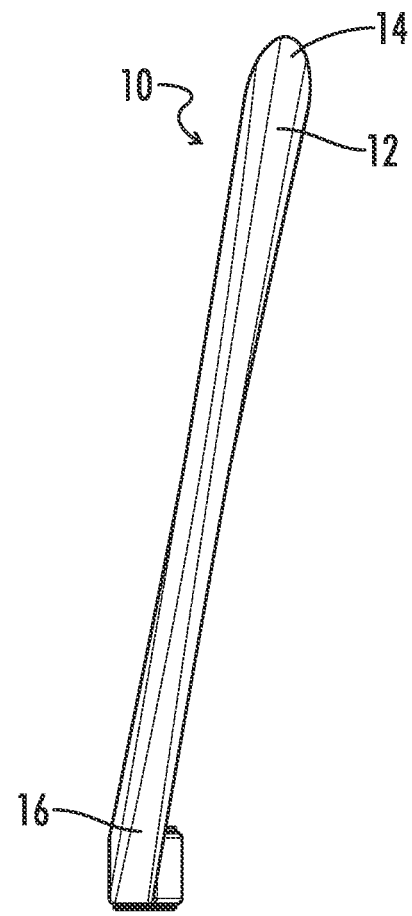
FIG. 11B shows a left side view of the handle with the insert of FIG. 8.
Figure 12:
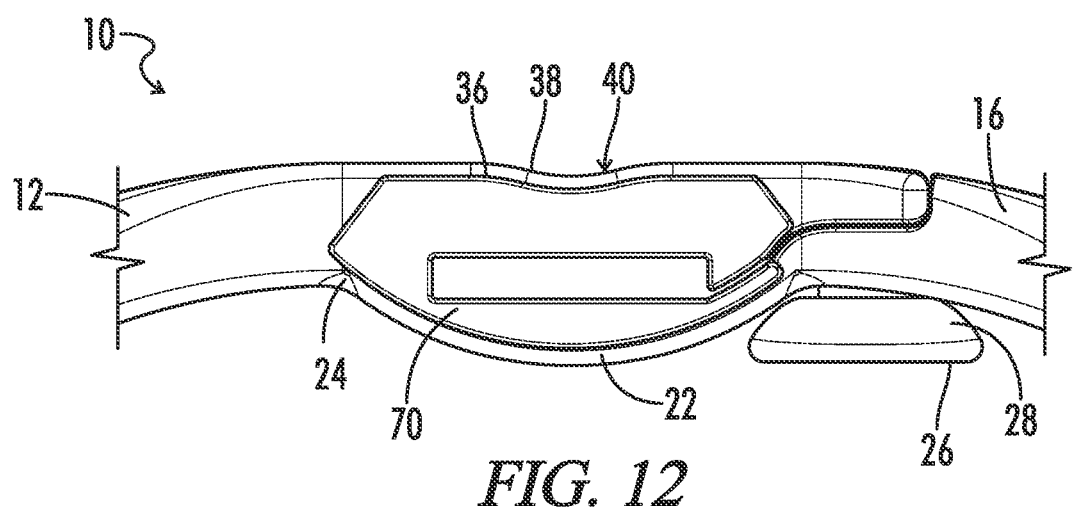
FIG. 12 shows a close-up top perspective view of the handle with the insert of FIG. 8.

The handle 10 may include a front cavity member 22 disposed on the front side 18 of the body 12 of the handle 10. The front cavity member 22 may be removable or partially removable, such as by being resiliently biased with the body 12 and pivotable along a hinge 24. As used herein, pivotable along the hinge 24 includes structural flex within the body 12 itself, even if no single pivot axis exists. The hinge 24 may be a pivot axis in the body 12 itself (e.g., a plastic hinge) or any suitable mechanical hinge, such as a butt hinge. The front cavity member 22 may be movable, such as pivotable, between a closed position (FIG. 2A) and an open position (FIG. 2B). The front cavity member 22 may extend outwardly (e.g., curve continuously) from the front side 18 of the handle 10.

A releasable fastener 26 may be disposed on the handle 10 and configured to secure the front cavity member 22 in the closed position. The releasable fastener 26 may be, for example, a thumb screw 28 and a cooperative threaded portion 30 or a friction fit. The front cavity member 22 may be configured to open away from the rear side 20 when moving from the closed position to the open position and toward the rear side 20 when moving from the open position to the closed position. The front cavity member 22 may include a first cavity end 32 and a second cavity end 34 opposite of the first cavity end 32.

The handle 10 includes a rear cavity member 36 opposite of the front cavity member 22. The rear cavity member 36 may be disposed on the rear side 20 of the body 12. The rear cavity member 36 may have an indentation 38 disposed on the rear side 20, such as an inwardly curving brace surface 40. Advantageously, the indentation 38 may enable a cooperative fit against a brace when the handle 10 is installed with the brace. The rear cavity member 36 may include an aperture 42 having the cooperative threaded portion 30. The rear cavity member 36 may be in a fixed position on the handle 10 such that when the front cavity member 22 is secured with the rear cavity member 36 via the releasable fastener 26, the front cavity member 22 is secured and the handle 10 is in the closed position.

The handle 10 includes a cavity 44 defined by the front cavity member 22 and the rear cavity member 36. The cavity 44 may be disposed at the bottom portion 16 of the body 12 of the handle 10. The cavity 44 may include a central longitudinal axis 46. The cavity 44 may have a semicircular profile, which enables the handle 10 to be used with a variety of types of knee braces, such as different models and those of different manufacturers.

The front cavity member 22 or the rear cavity member 36 may include one or more inner grooves 48. Advantageously, the one or more grooves 48 allow the handle 10 to be used in a variety of types of knee braces, such as different models and those of different manufacturers, such that the knee brace may be a universal handle 10 for knee braces, fitting the majority of makes and models of knee braces. The one or more grooves 48 of the front cavity member 22 may comprise a first groove 50 and a second groove 52 disposed proximate to a first cavity end 32 and a second cavity end 34, respectively, of the front cavity member 22. The first groove 50 and the second groove 52 of the front cavity member 22 may each have a triangular, hemispherical, or rectangular profile. The front cavity member 22 may include a third groove 54 and a fourth groove 56 disposed proximate to the first groove 50 and the second groove 52, respectively. The third groove 54 and the fourth groove 56 may be positioned inwardly from the first groove 50 and the second groove 52, respectively. The third and fourth grooves 54, 56 may be shallow in depth, particularly when compared to first and second grooves 50, 52. The third and fourth grooves 54, 56 may each have a triangular, hemispherical, or rectangular profile.

The one or more grooves 48 of the rear cavity member 36 may comprise a first groove 58 and a second groove 60 disposed proximate to, or at, a first cavity end 62 and a second cavity end 64, respectively, of the rear cavity member 36. The first and second grooves 58, 60 may each have a triangular, hemispherical, or rectangular profile. The rear cavity member 36 may include a third groove 66 and a fourth groove 68 disposed proximate to the central longitudinal axis 46. The third and fourth grooves 66, 68 may be evenly spaced a distance away from the central longitudinal axis 46. The third and fourth grooves 66, 68 may each have a triangular, hemispherical, or rectangular profile. It has been advantageously found that the profile of the cavity 44, particularly when combined with the one or more grooves 48, enable the cavity 44 to cooperatively receive a portion of a brace (particularly the structural support members of the brace, such as the linkages).

As shown in FIGS. 5-12, the handle 10 may include an insert 70 configured to be cooperatively received in the cavity 44. The insert 70 includes an insert body 72. The insert body 72 may be constructed of any suitable material, including polymers such as polyethylenes, polypropylene, polyvinyl chloride, polylactic acids, and acrylonitrile butadiene styrene, or metals or metal alloys, such as stainless steel. The insert body 72 may be constructed of a material that is antiallergenic. The insert body 72 may be impregnated with an antimicrobial, such as triclosan.

The insert body 72 may include outer sidewalls 74 that are shaped to be cooperatively received in the cavity 44 (including the one or more grooves 48) such that the insert 70 may be inserted into the cavity 44 when the front cavity member 22 is in the open position and secured within the cavity 44 when the front cavity member 22 is moved into, and secured in, the closed position. The insert 70 may have an insert top 76 and an insert bottom 78, with a slot 80 extending from, and thereby creating a passageway, from the insert top 76 to the insert bottom 78. The slot 80 may have a rectangular, triangular, oval, or circular inner profile. The profile of the slot 80 may be different than the inner profile of the cavity 44. Advantageously, insert 70 allows the handle 10 to be compatible with yet further models and makes of knee braces.

The insert 70 may have a moveable wall 82 so as to allow a portion of a knee brace to pass through to slot 80. The moveable wall 82 may be, for example, resiliently biased so that the wall 82 pivots along a hinge 84 to expand and close a gap 83. As used herein, pivots along the hinge 84 includes structural flex within the body 12 itself, even if no single pivot axis exists. Thus, the insert 70 may be transitioned between an open position (FIG. 6B) and a closed position (FIG. 6A), such as by moving the resiliently biased wall 82 outwardly and allowing the wall 82 to return the insert 70 to the closed position. A portion of the knee brace may be inserted into the slot 80 by this opening and closing of the insert 70.

The insert 70 may include an upper lip 86 and a bottom lip 88 disposed at the insert top 76 and the insert bottom 78, respectively. Upper lip 86 and bottom lip 88 may longitudinally secure the insert 70 when the insert 70 is positioned within the cavity 44, thereby preventing or resisting longitudinal disassociation with the cavity 44.

The handle body 12 and/or the insert body 72, including components thereof, may be rigid. The handle body 12 and/or the insert body 72, including components thereof, may be integrally formed.

While the exemplary embodiments of the handle 10 show the cavity 44 formed in the bottom portion 16, the cavity 44 and the associated features may be positioned in any suitable position on the handle 10. By way of example, the cavity 44, front cavity member 22, and rear cavity member 36 may be positioned on one or both of the legs 15, 17. Similarly, while the exemplary embodiments of the handle 10 show the cavity 44 and the associated features in a latitudinal orientation on the handle 10, the cavity 44 and the associated features (e.g., the members 22, 36) may be in a longitudinal orientation on the handle 10.

Also disclosed herewith are methods of using the handle 10 with a knee brace. The method includes providing the handle 10. The methods include opening the front member 22 and/or the insert 70 into the open position and securing a portion of the knee brace with the cavity 44 or the slot 80, respectively. When secured with the insert 70, transitioning the insert 70 into the closed position and positioning the insert 70 within the cavity 44. The front member 22 may be transitioned into a closed position and secured via the releasable fastener 26, such as screwing the thumb screw 28. The handle 10 is thereby attached to the portion of the knee brace and may be used by the subject. The method may include releasing the releasable fastener 26, such as unscrewing the thumb screw 28, and removing the portion of the knee brace from the insert 70 and/or the cavity 44.

Although embodiments of the disclosure have been described using specific terms, devices, and methods, such description is for illustrative purposes only. The words are words of description rather than of limitation. It is to be understood that changes and variations may be made by those of ordinary skill in the art without departing from the spirit or scope of the present disclosure, which is set forth in the following claims. It is further noted that any range provided herein provides support and a basis for any subset within that range. Further embodiments of the disclosure contain combinations, or exclusions, of different embodiments described herein.

Thus, although there have been described embodiments of the present invention of a new and useful handle, it is not intended that such references be construed as limitations upon the scope of this invention except as set forth in the following claims.

What is claimed is:
1. A handle for a knee brace, the handle comprising:
   a body including a top portion, a bottom portion opposite of the top portion, a front side, and a rear side opposite of the front side;
   a resiliently biased front cavity member disposed on the front side of the body and defining a hinge, wherein the resiliently biased front cavity member hingedly pivots between a closed cavity position and an open cavity position;

a rear cavity member disposed on the rear side of the body and opposite of the resiliently biased front cavity member;

a cavity defined by the resiliently biased front cavity member and the rear cavity member, the cavity having an inner profile;

a releasable fastener configured to secure the resiliently biased front cavity member in the closed cavity position, wherein either of the resiliently biased front cavity member or the rear cavity member include one or more inner grooves; and an insert configured to be cooperatively received in the cavity, the insert including a slot having a differing inner profile from the inner profile of the cavity, the insert comprising a resiliently biased hinge configured to move between a closed insert position and an open insert position.

2. The handle of claim 1, wherein the cavity is disposed at the bottom portion of the body.

3. The handle of claim 1, wherein the releasable fastener is a thumb screw or a friction fit.

4. The handle of claim 1, wherein the resiliently biased front cavity member is configured to open away from the rear side when moving from the closed cavity position to the open cavity position, and toward the rear side when moving from the open cavity position to the closed cavity position.

5. The handle of claim 1, wherein the resiliently biased front cavity member and the rear cavity member each include the one or more grooves.

6. The handle of claim 5, wherein the rear cavity member includes a first cavity end and a second cavity end opposite of the first cavity end, and wherein the rear cavity member includes a first groove and a second groove each having a triangular profile and disposed at the first cavity end and second cavity end, respectively.

7. The handle of claim 6, wherein the cavity includes a central longitudinal axis, and wherein the rear cavity member includes a third groove and a fourth groove disposed proximate to the central longitudinal axis, and wherein the third groove and the fourth groove each have a rectangular profile.

8. The handle of claim 5, wherein the resiliently biased front cavity member includes a first cavity end and a second cavity end opposite of the first cavity end, and wherein the one or more grooves of the resiliently biased front cavity member comprise a first groove and a second groove disposed proximate to the first cavity end and the second cavity end, respectively.

9. The handle of claim 8, wherein the first groove and the second groove of the resiliently biased front cavity member have a triangular profile.

10. The handle of claim 8, wherein the resiliently biased front cavity member includes a third groove and a fourth groove disposed proximate to the first groove and second groove, respectively, of the resiliently biased front cavity member.

11. The handle of claim 1, wherein the inner profile of the cavity comprises a semicircular profile.

12. The handle of claim 1, wherein the inner profile of the slot is rectangular.

13. The handle of claim 1, wherein the resiliently biased hinge of the insert is configured to open away from the rear side of the body when moving from the closed insert position to the open insert position, and toward the rear side of the body when moving from the open insert position to the closed insert position.

14. The handle of claim 1, wherein the insert includes an upper lip and a bottom lip.

15. The handle of claim 1, wherein the cavity includes a central longitudinal axis, and wherein the resiliently biased front cavity member curves away from the central longitudinal axis.

16. The handle of claim 1, wherein the body is rigid.

17. The handle of claim 1, wherein a rear side of the rear cavity member includes an indentation.

18. The handle of claim 1, wherein the body is elongated from the top portion to the bottom portion.

19. The handle of claim 1, wherein the body includes a first leg and a second leg extending from the top portion to the bottom portion, and wherein the top portion has a width that is greater than a width of the first leg and the second leg.

20. The handle of claim 1, wherein the body is integrally formed.

* * * * *